United States Patent
Riether et al.

(10) Patent No.: US 11,324,724 B2
(45) Date of Patent: May 10, 2022

(54) N-(2,2-DIFLUOROETHYL)-N-[(PYRIMIDINYLAMINO)PROPANYL] ARYLCARBOXAMIDES

(71) Applicant: Boehringer Ingelheim International GmbH, Ingelheim am Rhein (DE)

(72) Inventors: Doris Riether, Biberach an der Riss (DE); Niklas Heine, Biberach an der Riss (DE); Uta Friederike Lessel, Maselheim (DE); Stefan Scheuerer, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/650,903

(22) PCT Filed: Sep. 26, 2018

(86) PCT No.: PCT/EP2018/076108
§ 371 (c)(1),
(2) Date: Mar. 26, 2020

(87) PCT Pub. No.: WO2019/063605
PCT Pub. Date: Apr. 4, 2019

(65) Prior Publication Data
US 2020/0283418 A1    Sep. 10, 2020

(30) Foreign Application Priority Data

Sep. 28, 2017   (EP) .................................... 17193649

(51) Int. Cl.
| A61K 31/4192 | (2006.01) |
| A61K 31/506 | (2006.01) |
| A61P 25/00 | (2006.01) |
| C07D 403/12 | (2006.01) |

(52) U.S. Cl.
CPC ........ *A61K 31/4192* (2013.01); *A61K 31/506* (2013.01); *A61P 25/00* (2018.01); *C07D 403/12* (2013.01)

(58) Field of Classification Search
CPC .............. C07D 403/12; A61K 31/4192; A61K 31/506; A61P 25/00
See application file for complete search history.

(56) References Cited

U.S. PATENT DOCUMENTS

2015/0166523 A1   6/2015  Araki et al.

FOREIGN PATENT DOCUMENTS

| WO | 2003051872 A1 | 6/2003 |
| WO | 201150198 A1 | 4/2011 |
| WO | 201150200 A1 | 4/2011 |
| WO | 2013187466 | 6/2013 |
| WO | 2016034882 A1 | 3/2016 |
| WO | WO-2016034882 A1 * | 3/2016 .............. A61P 25/04 |
| WO | 2017129829 A1 | 8/2017 |
| WO | 2017139603 A1 | 8/2017 |
| WO | 2017178341 A1 | 10/2017 |

OTHER PUBLICATIONS

Johnson et al, Nature Medicine 2010, vol. 16(1), pp. 111-116. (Year: 2010).*
Bonaventure et al, Journal of Pharmacology and Experimental Therapeutics 2015, vol. 352, pp. 590-601. (Year: 2015).*
Suzuki, Discovery and in vitro and in vivo profiles, Bioorganic & Medicinal Chemistry 2015, vol. 23, p. 1260-1275.
Bonaventure et al., A selective Orexin-1 Receptor, J. Pharmacol. Exp. Ther., 2015, vol. 352, No. 3, p. 590-601.
Chen et al., The hypocretin.Orexin System, Med. Res. Rev., 2015, vol. 35, No. 1, p. 152-197.
Degorce et al. HTRF: A Technology Tailored for Drug Discovery, Curr. Chem. Genomics 2009, vol. 3, p. 22-32.
DeLecea et al., The hypocretins, Proc. Nat. Acad. Sci., 1998, vol. 95, No. 1, p. 322-327.
Gotter et al., International Union of Basic and Clinical Pharmacology, Pharmacol. Rev., 2012, vol. 64, p. 389-420.
International Search Report and Written Opinion for corresponding application, PCT/EP2018/076108, dated Jan. 2, 2019.
J. Med. Chem. 2015, vol. 59, p. 504-530.
Kishi et al., Suvorexant for Primary Insomnia, PLoS One, 2015; vol. 10, No. 8, e0136910.
Muschamp Hypocretins facilitates reward by atteniuating the antireward affects, Proc. Natl. Acad. Sci. USA, 2014, vol. 111, No. 16, p. E1648-1655.
Sakurai et al., The role of orexin in motivated behaviors, Cell, 1998, vol. 92, No. 4, p. 573-585.
Trinquet d-myo-Inositol 1-phosphate as a surrogate of d-myo-inositol 1.4.5 trisphosphate, et al. Anal. Biochem. 2006, vol. 358, p. 126-135.
Johnson, A key role for orexin in panic anxiety, Nature, vol. 16, 2010.
Sakurai et al., Cell, 1998, vol. 92, No. 4, p. 573-585.
DeLecea et al., Proc. Nat. Acad. Sci., 1998, vol. 95, No. 1, p. 322-327.
Muschamp et al., Proc. Natl. Acad. Sci. USA, 2014, vol. 111, No. 16, p. E1648-1655.
Sakurai et al., Nat. Rev. Neurosci., 2014, vol. 15, No. 11, p. 719-731.
Chen et al., Med. Res. Rev., 2015, vol. 35, No. 1, p. 152-197.
Gotter et al., Pharmacol. Rev., 2012, vol. 64, p. 389-420.
Kishi et al., PLoS One, 2015; vol. 10, No. 8, e0136910.
Bonaventure et al., J. Pharmacol. Exp. Ther., 2015, vol. 352, No. 3, p. 590-601.
Bioorganic & Medicinal Chemistry 2015, vol. 23, p. 1260-1275.
Trinquet et al. Anal. Biochem. 2006, vol. 358, p. 126-135.
Degorce et al. Curr. Chem. Genomics 2009, vol. 3, p. 22-32.

* cited by examiner

*Primary Examiner* — Craig D Ricci
*Assistant Examiner* — Janet L Coppins
(74) *Attorney, Agent, or Firm* — Shelley A. Jones

(57) ABSTRACT

The present invention relates to novel N-(2,2-difluoroethyl)-N-[(Pyrimidinylamino)propanyl]-arylcarboxamide derivatives, processes for their preparation, pharmaceutical compositions containing them and their use in therapy, particularly in the treatment or prevention of conditions having an association with the orexin sub-type 1 receptor.

8 Claims, No Drawings

N-(2,2-DIFLUOROETHYL)-N-[(PYRIMIDINYLAMINO)PROPANYL]ARYLCARBOXAMIDES

FIELD OF THE INVENTION

The present invention relates to novel N-(2,2-difluoroethyl)-N-[(pyrimidinylamino)propanyl]arylcarboxamide derivatives, processes for their preparation, pharmaceutical compositions containing them and their use in therapy, particularly in the treatment or prevention of conditions having an association with the orexin sub-type 1 receptor.

BACKGROUND OF THE INVENTION

Orexins are hypothalamic neuropeptides that play an important role in the regulation of many physiological behaviours such as arousal, wakefulness, appetite, food intake, cognition, motivated behaviours, reward, mood and stress. Orexin A, also referred to as hypocretin 1, is a peptide composed of 33 amino acids and orexin B, also referred to as hypocretin 2, is a peptide composed of 28 amino acids. Both are derived from a common precursor peptide referred to as pre-pro-orexin [Sakurai et al., Cell, 1998 Feb. 20; 92(4):573-85, and De Lecea et al., Proc. Nat. Acad. Sci., 1998 Jan. 6; 95(1):322-7). Orexins bind to two orphan G-protein-coupled receptors, the orexin receptor type 1 (OX1R) and orexin receptor type 2 (OX2R), which are widely distributed in the central nervous system and peripheral organs such as adrenal glands, gonads, and gut. Whereas orexin A binds predominantly to OX1R, orexin B is able to bind to both OX1R and OX2R.

Orexins are involved in the regulation of a wide range of behaviours including for example the regulation of emotion and reward, cognition, impulse control, regulation of autonomic and neuroendocrine functions, arousal, vigilance and sleep-wakefulness states (Muschamp et al., Proc. Natl. Acad. Sci. USA 2014 Apr. 22; 111(16):E1648-55; for a recent review see Sakurai, Nat. Rev. Neurosci., 2014; November; 15(11):719-31; Chen et al., Med. Res. Rev., 2015; January; 35(1):152-97; Gotter et al., Pharmacol. Rev., 2012, 64:389-420 and many more). Dual antagonism of OX1R and OX2R by small molecules is clinically efficacious in the treatment of insomnia, for which the drug suvorexant, [[(7R)-4-(5-chloro-1,3-benzoxazol-2-yl)-7-methyl-1,4-diazepan-1-yl][5-methyl-2-(2H-1,2,3-triazol-2-yl)phenyl]methanone] has been granted marketing authorisation (Kishi et al., PLoS One, 2015; 10(8):e0136910). The sleep-inducing effects of dual orexin receptor antagonists are predominantly mediated via OX2R (Bonaventure et al., J. Pharmacol. Exp. Ther., March 2015, 352, 3, 590-601), whereas the other physiological states such as emotion and reward, cognition, impulse control, regulation of autonomic and neuroendocrine functions, arousal, and vigilance are rather mediated via OX1R.

Due to their sleep-inducing effects, dual OX1R and OX2R antagonists are not suitable for treating disorders related to impulse control deficits as seen in addictions such as substance use disorders, personality disorders, such as borderline personality disorder, eating disorders such as binge eating disorder or attention deficit hyperactivity disorder. Therefore, it is desirable to provide an OX1R selective antagonist for the treatment of impulse control deficits.

Orexin receptor antagonists of various structural classes are reviewed in Roecker et al. (J. Med. Chem. 2015, 59, 504-530). WO03/051872, WO2013/187466, WO2016/034882, WO 2017/129829 and Bioorganic & Medicinal Chemistry 2015, 23, 1260-1275 describe orexin receptor antagonists.

DETAILED DESCRIPTION OF THE INVENTION

The present invention provides novel N-(2,2-difluoroethyl)-N-[(pyrimidinylamino)propanyl]arylcarboxamide derivatives that unexpectedly are highly potent OX1R antagonists (assay A) further characterized by
1) high selectivity over the OX2 receptor (assay B),
2) a medium to high stability in human liver microsomes (assay C), and
3) no or low MDCK (Madin-Darby canine kidney) efflux (assay D).

Compounds of the present invention are superior to those disclosed in the prior art in terms of the combination of the following key pharmacodynamic and pharmacokinetic parameters:
1) potency as OX1R antagonists,
2) selectivity over the OX2 receptor,
3) stability in human liver microsomes,
4) MDCK efflux, and
5) volume of distribution.

Stability in human liver microsomes refers to the susceptibility of compounds to biotransformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolization in vitro. Enhanced stability in human liver microsomes is associated with several advantages, including increased bioavailability and longer half-life, which can enable lower and less frequent dosing of patients. Thus, enhanced stability in human liver microsomes is a favorable characteristic for compounds that are to be used for drugs.

The MDCK assay provides information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction.

The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1 P-gp. Identical or similar permeabilities in both transport directions indicate passive permeation, vectorial permeability points to additional active transport mechanisms. Higher PEBA than PEAB (PEBA/PEAB>5) indicates the involvement of active efflux mediated by MDR1 P-gp, which might compromises the goal to achieve sufficient brain exposure. Therefore this assay provides valuable support for selection of compounds applicable for further in vivo testing. High permeability not limited by efflux at the blood brain barrier is a favourable characteristic for compounds that are to be used for drugs acting primarily in the CNS Compounds of the present invention differ structurally from Examples 84 and 91 in WO2016/034882 (the closest prior art compounds) in that they contain a central N-(2,2-difluoroethyl)-(propan-2-yl)amino moiety in place of the N-methyl-[butan-2-yl]amino moiety. These structural differences unexpectedly result in a superior combination of the following key pharmacodynamic and pharmacokinetic parameters:

1) potency as OX1R antagonists,
2) selectivity over the OX2 receptor,
3) stability in human liver microsomes,
4) MDCK efflux, and
5) volume of distribution.

Due to their high potency at OX1R and selectivity over OX2R, compounds of the present invention are expected to be both efficacious in in vivo models and to have a sufficient window between efficacy and undesired effects such as drowsiness or sleep.

Due to the superior combination of the key pharmacodynamic and pharmacokinetic parameters (#1-5) compounds of the present invention are expected to demonstrate adequate brain exposure and to have a medium to low in vivo clearance and thus a longer duration of action and higher tolerability. Consequently, compounds of the present invention must be more viable for human use.

General Definitions

Terms not specifically defined herein should be given the meanings that would be given to them by one skilled in the art in light of the disclosure and the context.
Stereochemistry:

Unless specifically indicated, throughout the specification and the appended claims, a given chemical formula or name shall encompass tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.
Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt with an acid. Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

Biological Assays

Abbreviations:
IP1 D-Myo-Inositol-1-phosphate
IP3 D-myo-inositol-1,4,5-triphosphate
HEPES 4-(2-hydroxyethyl)-1-piperazineethanesulfonic acid
HBSS Hanks' Balanced Salt Solution
BSA bovine serum albumin
DMSO dimethyl sulfoxide
CHO Chinese hamster ovary Activation of the orexin receptors expressed in cell lines results in an increase in intracellular IP3 concentration. IP1, a downstream metabolite of IP3, accumulates in cells following receptor activation and is stable in the presence of LiCl. Using Homogeneous Time-Resolved Fluorescence technology with Lumi4-Tb cryptate (commercially available from Cisbio Bioassay.) and a suitable fluorescence plate reader. This functional response is detectable and quantifiable as described in Trinquet et al. Anal. Biochem. 2006, 358, 126-135, Degorce et al. Curr. Chem. Genomics 2009, 3, 22-32. This technique is used to characterize pharmacological modification of the orexin receptors.

The biological activity of compounds is determined by the following methods:
A. In Vitro Testing of OX1R Potency: OX1R IP1

IP1 measurements are performed in CHO-K1 cells stably expressing the full-length human Orexin 1 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx1 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is re-suspended in medium and then distributed into the assay plates with a density of 10000 cells/25 µL per well. The plates are incubated for one hour at room temperature to reduce edge effects before they are incubated for 24 hours at 37° C./5% $CO_2$. Compounds are prepared by an 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 µL assay buffer (20 µL buffer remained in the wells after washing), followed by adding 5 µL per well of compounds diluted in assay buffer. After 15 minutes of incubation at room temperature 5 µL per well of Orexin A peptide (final concentration: 0.5 nM, and/or 50 nM) dissolved in assay buffer is added to the assay plate. The assay plate is incubated for 60 minutes at 37° C. Then 5 µl per well of Anti-IP1-Cryptate Tb solution and 5 µl per well of IP1-d2 dilution are added and the plate is incubated for a further 60 minutes light protected at room temperature. The emissions at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4),110-112).

B. In Vitro Testing of OX2R Potency: OX2R IP1

IP1 measurements are performed in CHO-K1 cells stably expressing the full-length human orexin 2 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOx2 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is resuspended in medium and then distributed into the assay plates with a density of 5000 cells/25 μper well. The plates are incubated for one hour at room temperature to reduce edge effects before they are incubated for 24 hours at 37° C./5% $CO_2$. Compounds are prepared by a 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay. On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM) dissolved in assay buffer is added to the assay plate. The assay plate is incubated for 60 minutes at 37° C. Then 5 μl per well of Anti-IP1-Cryptate Tb solution and 5 μl per well of IP1-d2 dilution are added to all well of the plate and the plate is incubated for a further 60 minutes light protected at room temperature. The emission at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4),110-112).

Kb values from Assay A (OX1R) and Assay B (OX2R) can then provide a selectivity ratio which is independent of the agonist (Orexin A) concentration.

C. Assessment of Metabolic Stability in Human Liver Microsomes (Human MST)

The metabolic stability of the compounds according to the invention may be investigated as follows:

The metabolic degradation of the test compound is assayed at 37° C. with pooled human liver microsomes. The final incubation volume of 100 μL per time point contains TRIS buffer pH 7.6 at room temperature (0.1 M), $MgCl_2$ (5 mM), microsomal protein (1 mg/mL) and the test compound at a final concentration of 1 μM. Following a short pre-incubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life ($t_{1/2}$) is determined by the slope of the semi-logarithmic plot of the concentration-time profile.

D. Assessment of Efflux in Madin-Darby Canine Kidney (MDCK) Cells Transfected with the Human MDR1 Gene Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2×10 e5 cells/1 cm2 area) are seeded on filter inserts (Costar transwell polycarbonate or PET filters, 0.4 μm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H2O$, 15 mM HEPES, 20 mM glucose, 0.25% BSA, pH 7.4) to prepare the transport solutions (0.1-300 μM compound, final DMSO<=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Biological Data

TABLE 1

In vitro potencies of the structurally closest prior art compounds (Example 91 and 84) in WO2016/034882 as reported therein:

| Structure Example # in WO2016/034882 | As described in WO2016/034882 (Table 1, Table 2, Table 3, page 177-180) | | |
|---|---|---|---|
| | OX1R | OX2R | OX2R $IC_{50}$/ OX1R $IC_{50}$ |
| Example 91 | Table 1 and 2: not reported Table 3: $pIC_{50} = 7.6$ corresponds to $IC_{50} = 25$ nM | Table 1 and 2: not reported Table 3: $pIC_{50} < 5.1$ corresponds to $IC_{50} = 7950$ nM | Table 3: 318 |
| Example 84 | Table 1 and 2: not reported Table 3: $pIC_{50} = 8.7$ corresponds to $IC_{50} = 1.9$ nM | Table 1 and 2: not reported Table 3: $pIC_{50} = 6.0$ corresponds to $IC_{50} = 1000$ nM | Table 3: 526 |

Compounds of the Present Invention

A full and detailed comparison of the key biological properties (including OX1R and OX2R potencies, stability in human liver microsomes and MDCK efflux) of all compounds of the present invention with the corresponding closest prior art compounds in WO2016/034882 respectively is shown in Table 1.

TABLE 2

Comparison of biological data of the compounds of the present invention with the closest prior art compounds in WO2016/034882

| Example | Structure | Assay A OX1R Kb [nM] (0.5 nM Orexin A concentration) | Assay B OX2R Kb [nM] (0.5 nM Orexin A concentration) | OX2R Kb/ OX1R Kb | Assay C: Human MST $t_{1/2}$ [min] | Assay D: MDCK efflux ratio (BA/AB) |
|---|---|---|---|---|---|---|
| Ex 91 in WO2016/ 034882 | 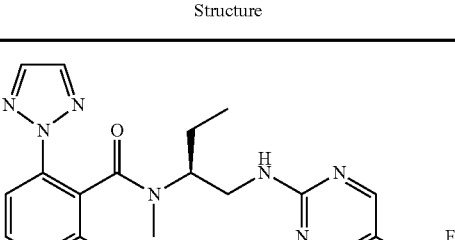 | 3.63 | 313 | 86 | >130 | <3 |

TABLE 2-continued

Comparison of biological data of the compounds of the present invention with the closest prior art compounds in WO2016/034882

| Example | Structure | Assay A OX1R Kb [nM](0.5 nM Orexin A concentration) | Assay B OX2R Kb [nM] (0.5 nM Orexin A concentration) | OX2R Kb/ OX1R Kb | Assay C: Human MST $t_{1/2}$ [min] | Assay D: MDCK efflux ratio (BA/AB) |
|---|---|---|---|---|---|---|
| 1 | 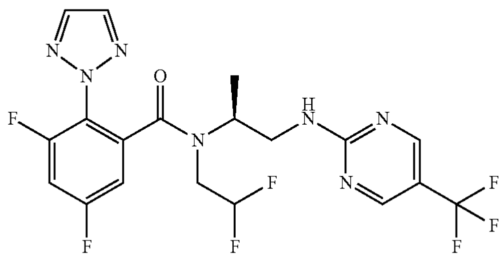 [SMILES: C[C@@H](CNc1ncc(C(F)(F)F)cn1)N(CC(F)F)C(=O)c1cc(F)cc(F)c1-n1nccn1] | 1.17 | 251 | 214 | >130 | <3 |
| 2 | 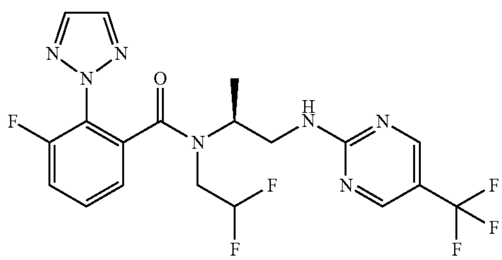 [SMILES: C[C@@H](CNc1ncc(C(F)(F)F)cn1)N(CC(F)F)C(=O)c1cccc(F)c1-n1nccn1] | 0.63 | 87.1 | 138 | >130 | <3 |
| Ex 84 in WO2016/ 034882 | 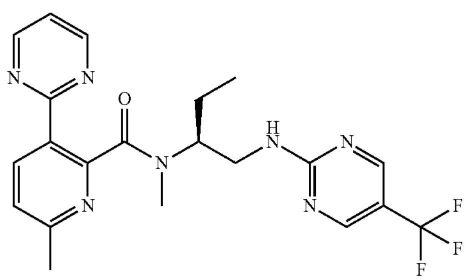 [SMILES: CC[C@@H](CNc1ncc(C(F)(F)F)cn1)N(C)C(=O)c1nc(C)ccc1-c1ncccn1] | 2.20 | 229 | 104 | 41 | <3 |
| 3 | 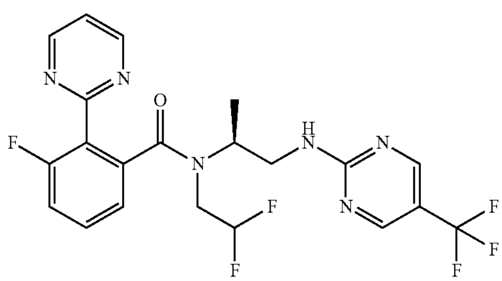 [SMILES: C[C@@H](CNc1ncc(C(F)(F)F)cn1)N(CC(F)F)C(=O)c1cccc(F)c1-c1ncccn1] | 0.19 | 108 | 568 | >130 | <3 |
| 4 | 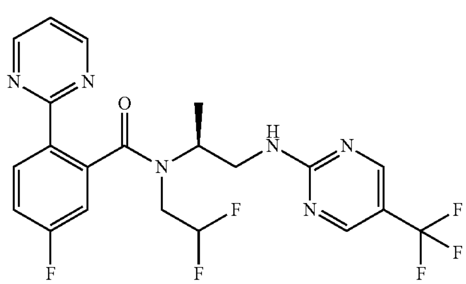 [SMILES: C[C@@H](CNc1ncc(C(F)(F)F)cn1)N(CC(F)F)C(=O)c1cc(F)ccc1-c1ncccn1] | 0.42 | 70.8 | 169 | >130 | <3 |

TABLE 2-continued

Comparison of biological data of the compounds of the present invention with the closest prior art compounds in WO2016/034882

| Example | Structure | Assay A OX1R Kb [nM](0.5 nM Orexin A concentration) | Assay B OX2R Kb [nM] (0.5 nM Orexin A concentration) | OX2R Kb/ OX1R Kb | Assay C: Human MST $t_{1/2}$ [min] | Assay D:MDCK efflux ratio (BA/AB) |
|---|---|---|---|---|---|---|
| 5 | (structure) | 0.67 | 143 | 213 | >130 | <3 |

Examples 1 and 2 of the present invention differ structurally from Example 91 in WO2016/034882 i.e. the closest prior art compound in that it contain a central N-(2,2-difluoroethyl)-(propan-2-yl)amino moiety in place of the N-methyl-[butan-2-yl]amino moiety. Furthermore, Example 1 contains two fluorine atoms with a different substitution pattern at the phenyl ring, while Example 2 contains one fluorine atom in a different position at the phenyl ring. These structural differences unexpectedly result in Examples 1 and 2 being more potent at OX1R and more selective, with comparable metabolic stability in human liver microsomes and MDCK efflux when compared to Example 91 in WO2016/034882.

Examples 3, 4 and 5 of the present invention differ structurally from Example 84 in WO2016/034882, i.e. the closest prior art compound in that they contain a central N-(2,2-difluoroethyl)-(propan-2-yl)amino moiety in place of the N-methyl-[butan-2-yl]amino moiety. Furthermore, they contain differently substituted phenyl ring with a fluorine atom instead of a methyl-substituted pyridyl ring. These structural differences unexpectedly result in Examples 3, 4 and 5 demonstrating higher potency and increased selectivity, and significantly better stability in human liver microsomes with comparable MDCK efflux when compared to Example 84 in WO2016/034882.

These results demonstrate that compounds of the present invention unexpectedly are more potent OX1R antagonists, with comparable or higher microsomal stability, and are more selective over the OX2 receptor than the structurally most similar example disclosed in WO2016/034882 (closest prior art compounds), respectively.

Use in Treatment/Method of Use

The present invention is directed to compounds which are useful in the treatment of a disease, disorder and condition wherein the antagonisms of OX1R is of therapeutic benefit, including but not limited to the treatment and/or prevention of psychiatric and neurological conditions associated with impulse control deficits. Such impulse control deficits are seen in addictions including substance use disorders; personality disorders such as borderline personality disorder; eating disorders such as binge eating disorder; or attention deficit hyperactivity disorder. According to a further aspect of the invention, compounds of the present invention are useful in the treatment of OX1R related pathophysiological disturbances in arousal/wakefulness, appetite/food intake, cognition, motivated behaviours/reward, mood and stress.

In view of their pharmacological effect, compounds of the present invention are suitable for use in the treatment of a disease or condition selected from the list consisting of (1) treatment or prevention of substance abuse/dependence/seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics, (2) eating disorders, such as binge eating, bulimia nervosa, anorexia nervosa, other specified feeding or eating disorders, obesity, overweight, cachexia, appetite/taste disorders, vomiting, nausea, Prader-Willi-Syndrome, hyperphagia, appetite/taste disorders, (3) attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la Tourette's syndrome, restless legs syndrome, dementia, dyskinesia, severe mental retardation, neurodegenerative disorders including nosological entities such as disinhibition-dementia-parkinsonism-amyotrophy complex, pallido-ponto-nigral degeneration, (4) cognitive dysfunction in psychiatric or neurological disorder, cognitive impairments associated with schizophrenia, Alzheimer's disease and other neurological and psychiatric disorders, (5) mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, (6) sexual disorder, sexual dysfunction, psychosexual disorder, (7) impulse control disorders such as pathological gambling, trichotillomania, intermittent explosive disorder, kleptomania, pyromania, compulsive shopping, internet addiction, sexual compulsion, (8) sleep disorders such as narcolepsy, jetlag, sleep apnea, insomnia, parasomnia, disturbed biological and circadian rhythms, sleep disturbances associated with psychiatric and neurological disorders, (9) treatment, prevention and relapse control of impulsivity and/or impulse control deficits and/or behavioural disinhibition in any psychiatric and/or neurological condition,

(10) personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders

(11) neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole. Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

Antidepressants
Mood stabilizers
Antipsychotics
Anxiolytics
Antiepileptic drugs
Sleeping agents
Cognitive enhancer
Stimulants
Non-stimulant medication for attention deficit hyperactivity disorder
Additional psychoactive drugs.

EXPERIMENTAL SECTION

List of Abbreviations

RT room temperature
ESI-MS electrospray ionisation mass spectrometry
aq. aqueous
MS mass spectrometry
MeOH methanol
PE petroleum ether
EA ethyl acetate
DMF N,N-dimethylformamide
DMSO dimethyl sulfoxide
DCM dichloromethane
DMA N,N-dimethylacetamide
TEA triethylamine
THF tetrahydrofuran
TBME tert-butyl-methyl-ether
DIPEA N,N-diisopropylethylamine
DIAD diisopropyl azodicarboxylate
CIP 2-chloro-1,3-dimethylimidazolidinium hexafluorophosphate
Rt retention time
h hour(s)
min minutes
ACN acetonitrile
TFA trifluoroacetic acid
M Molarity
N normality
HPLC high-performance liquid chromatography
NMP N-methyl-2-pyrrolidon
TLC Thin layer chromatography HPLC-Methods:

Method Name: A
Column: BEH C18 1.7 μm 2.1×50 mm
Column Supplier: Waters

| Gradient/Solvent Time [min] | % Sol [90% H$_2$O + 10% ACN + NH$_4$COOH 5 mM] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: B
Column: Xselect CSH, 2.5 μm, 4.6×50 mm
Column Supplier: Waters

| Gradient/Solvent Time [min] | % Sol [90% H$_2$O + 10% ACN + 0.1% HCOOH] | % Sol [90% ACN + 10% H$_2$O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: C
Column: Xselect CSH Phenyl-Hexyl, 4.6×50 mm, 2.5 μm,
Column Supplier: Waters

| Gradient/Solvent Time [min] | % Sol [90% H₂O + 10% ACN + 0.1% HCOOH] | % Sol [90% ACN + 10% H₂O] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

Method Name: D
Column: Venusil, 2.1×50 mm, 5 μm
Column Supplier: Agilent Technologies

| Gradient/Solvent Time [min] | % Sol [H₂O, 0.0675% TFA] | % Sol [ACN, 0.0625% TFA] | Flow [mL/min] | Temp [° C.] |
|---|---|---|---|---|
| 0.00 | 100 | 0 | 0.8 | 40 |
| 4.40 | 70 | 30 | 0.8 | 40 |
| 5.20 | 70 | 30 | 0.8 | 40 |
| 5.22 | 100 | 0 | 0.8 | 40 |
| 5.90 | 100 | 0 | 0.8 | 40 |

Method Name: E
Column: Venusil, 2.1×50 mm, 5 μm
Column Supplier: Agilent Technologies

| Gradient/Solvent Time [min] | % Sol [H₂O, 0.0375% TFA] | % Sol [ACN, 0.0018% TFA] | Flow [mL/min] | Temp [° C.] |
|---|---|---|---|---|
| 0.00 | 90 | 10 | 1.0 | 50 |
| 2.00 | 20 | 80 | 1.0 | 50 |
| 2.48 | 20 | 80 | 1.0 | 50 |
| 2.50 | 90 | 10 | 1.0 | 50 |
| 3.00 | 90 | 10 | 1.0 | 50 |

Preparation of Intermediates

Acid Intermediates

| Acid | Name | Structure | Reference/source |
|---|---|---|---|
| A-1 | 3-Fluoro-2-[1,2,3]triazol-2-yl-benzoic acid | 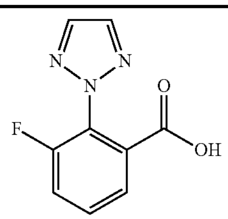 | WO2011/50198, Page 47, Intermediate 5 |
| A-2 | 3-Fluoro-2-pyrimidin-2-yl-benzoic acid | 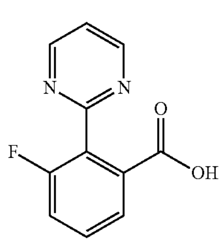 [SMILES: O=C(O)c1cccc(F)c1-c1ncccn1] | WO2011/50200, page 78, Intermediate 52 |
| A-3 | 3,5-Difluoro-2-[1,2,3]triazol-2-yl-benzoic acid | | WO2011/50198, Page 64, Compound (w); See also in PCT/EP2017/058318 |

2-Fluoro-6-Pyrimidin-2-Yl-Benzoic Acid A-4

A-4 is prepared in analogy to the above described procedure. ESI-MS: 219 [M+H]⁺; HPLC (Rt): 0.93 min (Method E).

5-Fluoro-2-Pyrimidin-2-Yl-Benzoic Acid A-5:

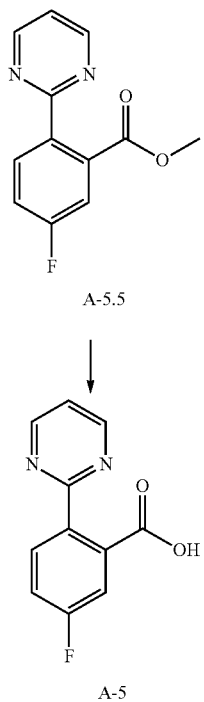

KOAc (32.8 g, 317.4 mmol) in dioxane is stirred under a nitrogen atmosphere for 2 h at 100° C. The reaction mixture is filtered through celite and extracted with EA. The organic phase is washed with H₂O, dried and evaporated. The crude product is purified by flash column chromatography on silica gel (using cyclohexane/EA 100/0 to 80/20) to provide 22 g of A-5.3. TLC (Rf): 0.3 (silica gel; cyclohexane/EA 9/1).

Step 2: A mixture of A-5.3 (12.0 g, 38.6 mmol), A-5.4 (5.4 g, 46.3 mmol), PdCl₂(dppf) (1.37 g, 1.66 mmol) and Na₂CO₃ (13.3 g, 124.4 mmol) in a mixture of 2-methyl-THF and H₂O is stirred under a nitrogen atmosphere at 80° C. overnight. The reaction mixture is treated with TBME and H₂O and filtered through celite. The organic phase is separated, dried and evaporated. The crude product is purified by flash column chromatography on silica gel (using PE/EA 3/1) to provide 7.0 g of A-5.5. TLC (Rf): 0.3 (silica gel; cyclohexane/EA 6/4).

Step 3: To a mixture of A-5.5 (3.5 g, 16.6 mmol) in a 3:1 mixture of 2-methyl-THF and H₂O (50 mL) NaOH (1.5 g, 36.6 mmol) is added and stirred at 70° C. for 2 h. The organic phase is separated and the aqueous phase is extracted with TBME. The aqueous phase is acidified with HCl, (36% aq. solution) to pH 1 and the precipitate is filtered off. The crude product is purified by flash column chromatography on silica gel (using DCM/MeOH 20/1) to provide 2.1 g of A-5. ESI-MS: 219 [M+H]⁺; HPLC (Rt): 3.42 min (method D).

Synthesis of Amine Intermediates

Step 1: A mixture of A-5.1 (20.0 g, 81.5 mmol), A-5.2 (25.0 g, 93.5 mmol), PdCl₂(dppf) (3.7 g, 4.3 mmol) and N—((S)-2-Amino-1-methyl-ethyl)-N-(2,2-difluoro-ethyl)-3-fluoro-2-pyrimidin-2-yl-benzamide B-1

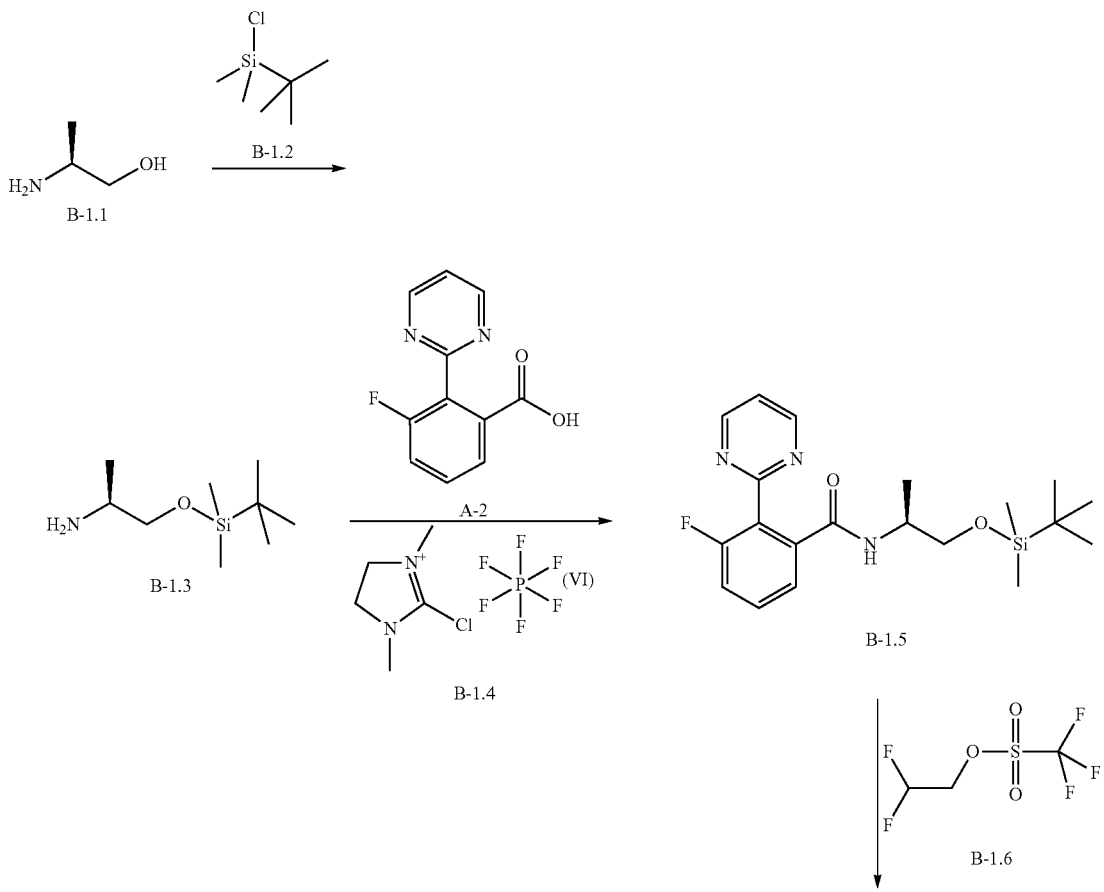

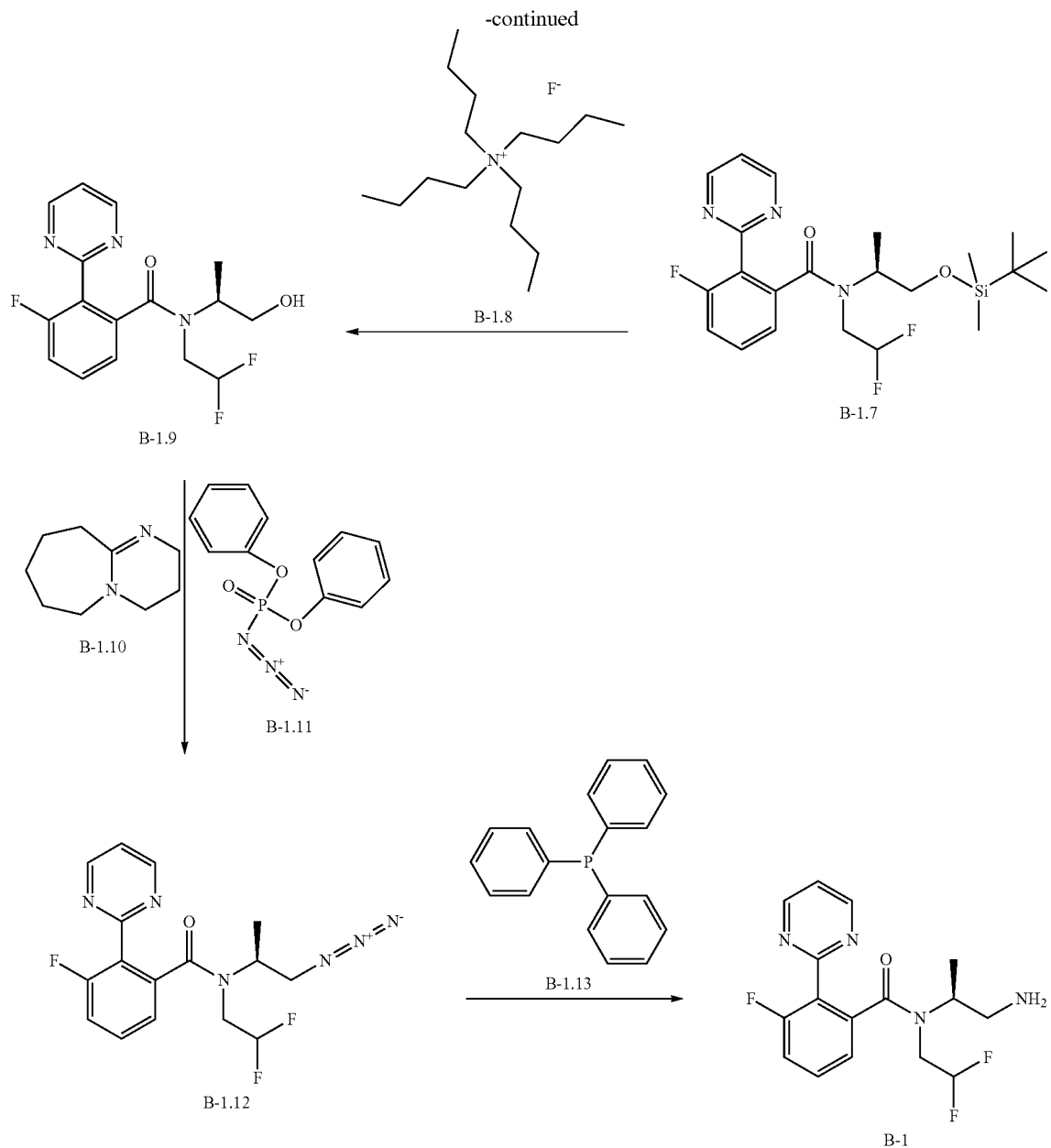

Step 1: A solution of TEA (11.1 mL; 79.9 mmol) in dry DCM (15.0 mL) is added dropwise to a solution of B-1.1 (3.0 g, 39.9 mmol) and B-1.2 (6.0 g, 39.9 mmol) in dry DCM (15.0 mL) under stirring. The reaction mixture is stirred at RT overnight. To the reaction mixture a saturated aq. $NH_4Cl$ solution (15.0 mL) is added and extracted with DCM. The organic phase is separated, dried and evaporated to get 7.0 g of B-1.3. ESI-MS: 189 [M+H]$^+$; HPLC (Rt): 0.86 min (method A).

Step 2: To a mixture of A-2 (2.1 g, 9.6 mmol), B-1.3 (2.0 g, 10.6 mmol) and DIPEA (3.6 mL, 21.0 mmol) in dry DMA and dry ACN under a nitrogen atmosphere B-1.4 (4.7 g, 16.9 mmol) is added and the reaction mixture is stirred at RT for 5 h. The reaction mixture is poured into cold $H_2O$ and extracted with EA. The organic phase is washed with diluted citric acid, dried and concentrated. The crude product is purified by flash column chromatography on silica gel (using EA/n-hexane/MeOH 80/20/1) to provide 600 mg of B-1.5. ESI-MS: 389 [M+H]$^+$; HPLC (Rt): 1.30 min (method A).

Step 3: To B-1.5 (670 mg, 3.66 mmol) in dry DMF (9.0 mL) NaH (110 mg, 2.75 mmol) is added at 0° C. After 30 min B-1.6 (710 mg, 1.82 mmol) is added at 0° C. The reaction mixture is warmed to RT and stirred 16 h. The reaction mixture is poured into cold $NH_4Cl$ solution and extracted with EA. The organic phase is separated, dried and evaporated. The crude product is purified by flash column chromatography on silica gel (using n-hexane/EA 80/20) to provide 670 mg of B-1.7. ESI-MS: 453 [M+H]$^+$; HPLC (Rt): 1.59 min (method A).

Step 4: To B-1.7 (660 mg, 1.46 mmol) in dry THF (9.0 mL) B-1.8 (1.6 mL, 1.60 mmol) is added under stirring at 0° C. The reaction mixture is stirred at 0° C. for 1 h. The solvent is evaporated and the crude product is purified by flash column chromatography on silica gel (using DCM/MeOH 97/3) to provide 450 mg of B-1.9. ESI-MS: 339 [M+H]+; HPLC (Rt): 0.76 min (method A).

Step 5: To B-1.9 (370 mg, 7.09 mmol) and B-1.10 (330 μL, 2.21 mmol) in dry THF (3.6 mL) B-1.11 (350 μL, 1.62 mmol) is added dropwise under a nitrogen atmosphere. The reaction mixture is stirred at RT for 16 h. The solvent is evaporated and the crude product is purified by flash column chromatography on silica gel (using EA/n-hexane/MeOH 40/60/1) to provide 270 mg of B-1.12. ESI-MS: 364 [M+H]+; HPLC (Rt): 1.03 min (method A).

Step 6: To B-1.12 (260 mg, 0.71 mmol) in THF (15.0 mL) and H₂O (0.8 mL) B-1.13 (500 mg, 1.91 mmol) is added under a nitrogen atmosphere and the reaction mixture is stirred at RT for 16 h. The reaction mixture is evaporated and the residue is treated with HCl (1 M, aq. solution) and extracted with EA. The organic phase is separated. The aqueous phase is basified with NH₄OH to pH 10-11 and extracted with DCM. The organic phase is dried and evaporated to get 240 mg of B-1. ESI-MS: 338 [M+H]+; HPLC (Rt): 0.62 min (method A).

(S)—N*2*-(Difluoroethyl)-N*1*(5-trifluoromethyl-pyrimidin-2-yl)-propane-1,2-diamine B-2

(180 mL) is added dropwise at 0° C. under N₂ atmosphere DIAD (3.0 mL, 16.6 mmol). The reaction mixture is warmed to RT and stirred for 16 h. The reaction mixture is concentrated and the residue is treated with water and extracted with EA. The organic layer is separated, dried and concentrated. The residue is purified by flash column chromatography on silica gel (using a solvent mixture of n-hexane/EA 70/30) to get 3.4 g of B-2.3. ESI-MS: 304 [M+H]+; HPLC (Rt): 1.06 min (method A).

Step 2: To B-2.3 (2.3 g, 7.56 mmol) and B-1.6 (1.2 mL, 8.97 mmol) in dry DMF NaH (60%, 340 mg, 8.50 mmol) is added at 0° C. and under a nitrogen atmosphere. The reaction mixture is stirred at RT for 16 h. The reaction mixture is poured into cold NH₄Cl (aq. solution) and extracted with EA. The organic phase is washed with H₂O, dried and evaporated. The residue is purified by flash column chromatography on silica gel (using a solvent mixture of n-hexane/EA 80/20) to get 1.6 g of B-2.4. ESI-MS: 368; TLC (Rf): 0.6 (silica gel; PE/EA 5/1).

Step 3: A mixture of B-2.4 (13.5 g, 36.5 mmol) and hydrazine hydrate (9.30 g, 182.7 mmol) in EtOH (150 mL) is stirred at RT for 20 h. The reaction mixture is filtered and

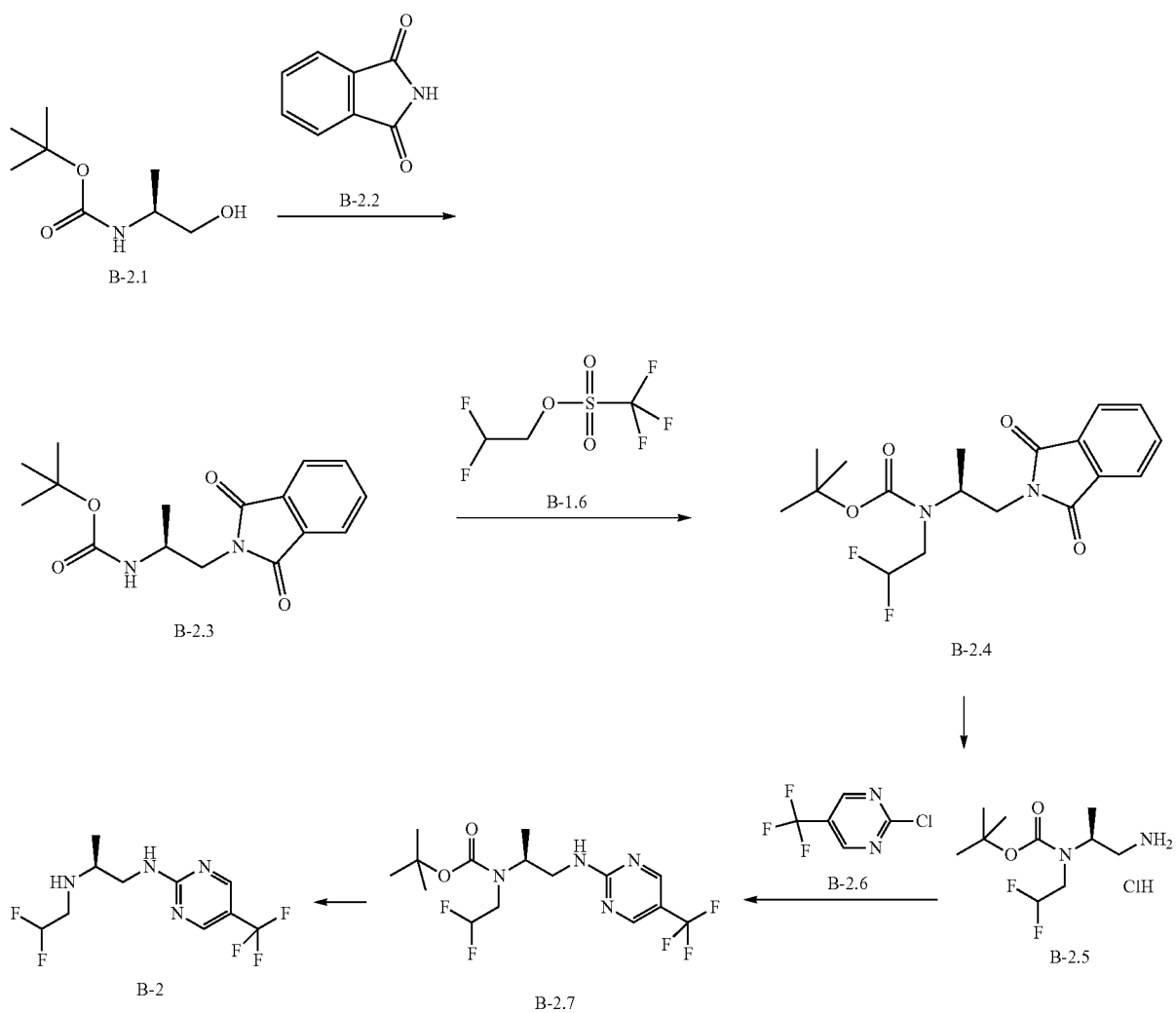

Step 1: To a mixture of B-2.1 (2.0 g, 11.4 mmol), B-2.2 (2.2 g, 14.9 mmol) and PPh₃ (3.9 g, 14.9 mmol) in dry THF the filtrate is evaporated. The residue is dissolved in H₂O and extracted with EA. The aqueous phase is acidified with HCl (0.05 M, aq. solution) to pH 6 and filtered. The filtrate is lyophilized to get 8.5 g of B-2.5. ESI-MS: 239; TLC (Rf): 0.5 (silica gel; PE/EA 5/1).

Step 4: To B-2.5 (4.0 g, 14.6 mmol) and DIPEA (2.74 mL, 16.0 mmol) in dry NMP (25.0 mL) B-2.6 (2.7 g, 14.6 mmol) is added and the reaction mixture is stirred in a microwave at 100° C. for 1 h. The reaction mixture is poured into H$_2$O and extracted with EA. The organic phase is washed with diluted citric acid (aq. solution), dried and evaporated. The residue is purified by flash column chromatography on silica gel (using a solvent mixture of cyclohexane/EA 95/5-60/40) to get 2.9 g of B-2.7. ESI-MS: 384 [M+H]$^+$; HPLC (Rt): 1.32 min (method A).

Step 5: To B-2.7 (2.9 g, 7.52 mmol) in dry 1,4-dioxane (5.0 mL) HCl (4 M in dioxane, 10.0 mL, 40.0 mmol) is added and the reaction mixture is stirred at RT overnight. The solvent is removed under reduced pressure, the residue is treated with H$_2$O and NH$_4$OH and extracted with DCM. The organic phase is dried and evaporated to get 2.1 g of B-2. ESI-MS: 284 [M+H]$^+$; HPLC (Rt): 1.01 min (method A).

Preparation of Compounds of the Present Invention

Example 2

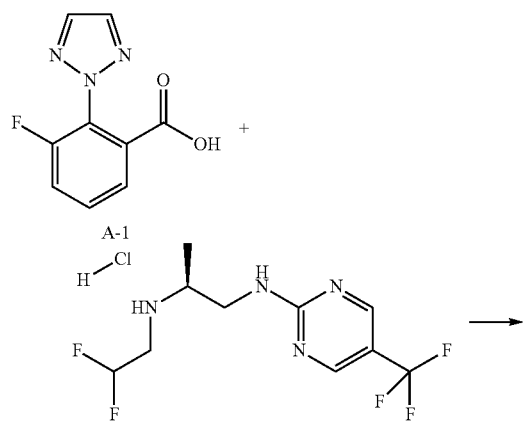

CIP (65 mg, 0.23 mmol) is added to a stirred mixture of A-1 (50 mg, 0.24 mmol), B-2 (65 mg, 0.20 mmol) and DIPEA (110 µL, 0.64 mmol) in dry ACN (2.0 mL) and the reaction mixture is stirred at RT overnight. The reaction mixture is filtered and purified by preparative LCMS (using a solvent gradient H$_2$O/ACN with NH$_4$OH) to afford 50 mg of compound Example 2. ESI-MS: 474 [M+H]$^+$; HPLC (Rt): 3.59 min (method B).

Example 3

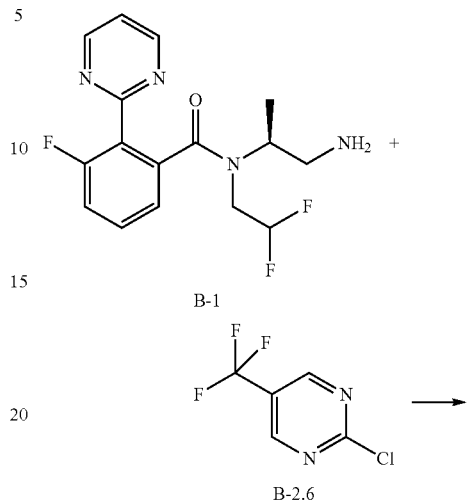

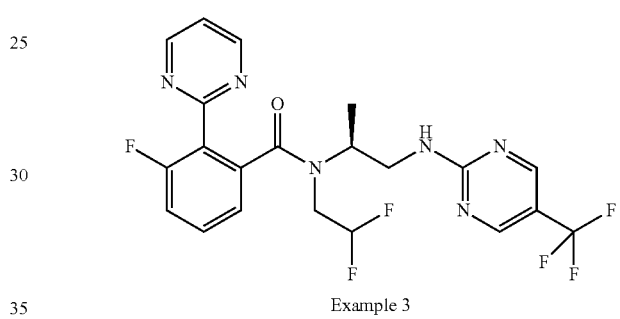

To a stirred mixture of B-1 (730 mg, 2.16 mmol) and B-2.6 (510 mg, 2.79 mmol) in NMP (10 mL) DIPEA (520 µL, 3.04 mmol) is added at RT under a nitrogen atmosphere. The reaction is heated at 100° C. for 1 h. After cooling the reaction is poured into water an extracted with EA.

The organic layer is separated, washed with citric acid (diluted aq. solution), dried and concentrated. The residue is purified by flash column chromatography on silica gel (using a solvent mixture DCM/MeOH 97/3) to afford 820 mg of Example 3. ESI-MS: 484 [M+H]$^+$; HPLC (Rt): 3.25 min (method C).

Example 4

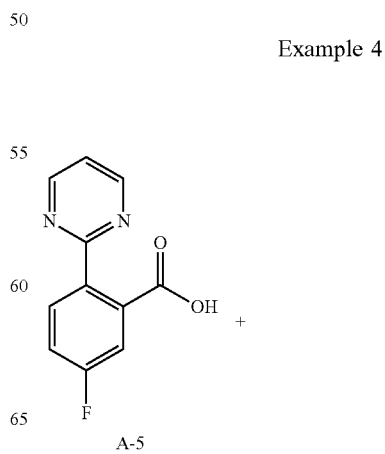

-continued

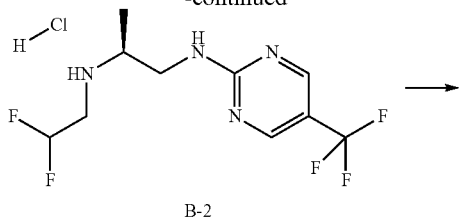

B-2

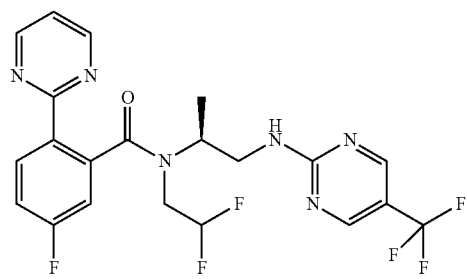

Example 4

DIPEA (120 μL, 0.70 mmol) is added to a stirred mixture of A-5 (100 mg, 0.35 mmol) and B-2 (90 mg, 0.41 mmol) in dry DMA at RT. After 20 min CIP (130 mg, 0.47 mmol) is added and the reaction mixture is stirred at 50° C. for 5 h before being cooled to RT and left stirring overnight. The mixture is treated with H$_2$O and extracted with EA. The organic phase is washed with H$_2$O, dried and evaporated. The residue is purified by preparative LCMS (using a solvent gradient H$_2$O/ACN with NH$_4$OH) to afford 60 mg of compound Example 4. ESI-MS: 485 [M+H]$^+$; HPLC (Rt): 3.53 min (method C).

The following example is prepared in analogy to the above described procedure using the corresponding acid (see Acid Intermediates) and amine (see Amine Intermediates) as described before. For Example 1: the reaction is carried out at RT overnight.

The invention claimed is:

1. A compound selected from the group consisting of:

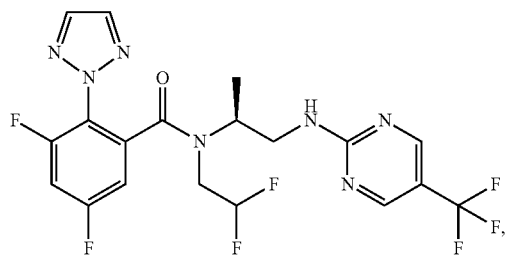

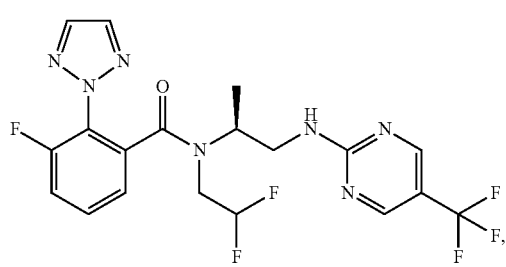

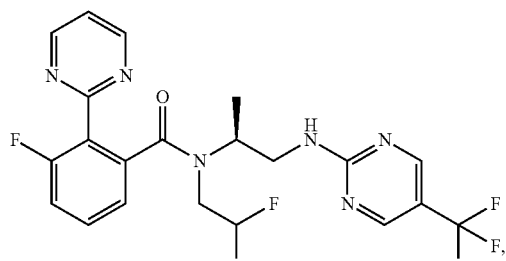

| Example | Structure | ESI-MS [M + H]$^+$ | HPLC (Rt) [min] | HPLC Method |
|---------|-----------|---------------------|------------------|-------------|
| 1 | 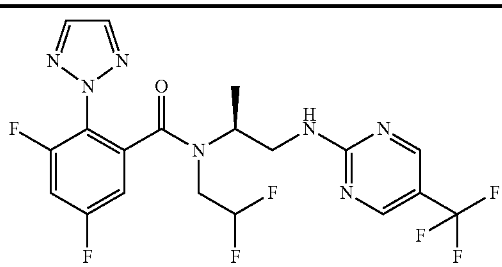 | 492 | 3.63 | C |
| 5 | 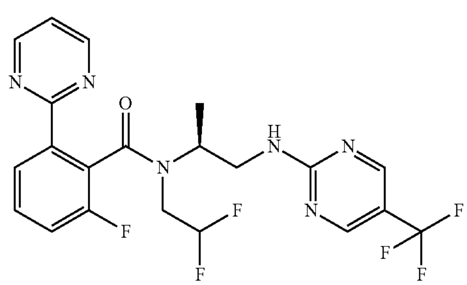 [SMILES: C[C@@H](CNc1ncc(C(F)(F)F)cn1)N(CC(F)F)C(=O)c1c(F)cccc1-c1ncccn1] | 485 | 3.72 | C |

-continued

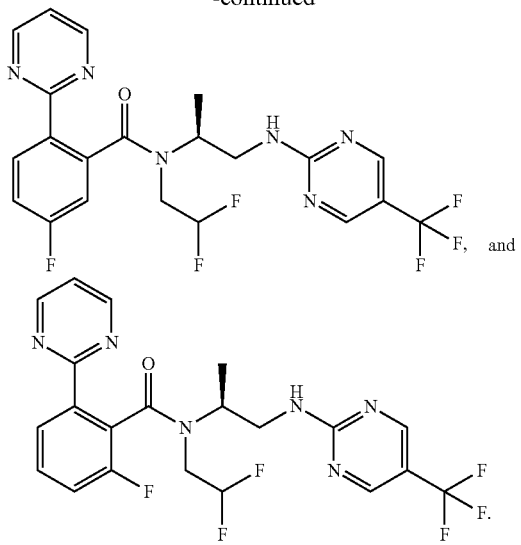

2. A pharmaceutically acceptable salt of the compound according to claim 1.

3. A pharmaceutical composition comprising the compound of claim 1 in an admixture with a pharmaceutically acceptable adjuvant.

4. A pharmaceutical composition comprising the compound of claim 1 in an admixture with a pharmaceutically acceptable diluent.

5. A pharmaceutical composition comprising the compound of claim 1 in an admixture with a pharmaceutically acceptable carrier.

6. A pharmaceutical composition comprising the compound of claim 2 in an admixture with a pharmaceutically acceptable adjuvant.

7. A pharmaceutical composition comprising the compound of claim 2 in an admixture with a pharmaceutically acceptable diluent.

8. A pharmaceutical composition comprising the compound of claim 2 in an admixture with a pharmaceutically acceptable carrier.

* * * * *